(12) United States Patent
Old et al.

(10) Patent No.: US 7,662,850 B2
(45) Date of Patent: *Feb. 16, 2010

(54) THERAPEUTIC SUBSTITUTED CHLOROCYCLOPENTANOLS

(75) Inventors: David W. Old, Irvine, CA (US); Vinh X. Ngo, Huntington Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/111,727

(22) Filed: Apr. 29, 2008

(65) Prior Publication Data

US 2009/0018168 A1    Jan. 15, 2009

Related U.S. Application Data

(60) Provisional application No. 60/949,627, filed on Jul. 13, 2007.

(51) Int. Cl.
*A61K 31/381*    (2006.01)
*C07D 333/04*   (2006.01)
(52) U.S. Cl. .................................. 514/448; 549/71
(58) Field of Classification Search ............ 549/29, 549/70, 71; 514/183, 430, 438, 448
See application file for complete search history.

(56) References Cited

U.S. PATENT DOCUMENTS 7,091,231 B2    8/2006   Donde
7,429,669 B2 *  9/2008   Old et al. ................... 549/64

OTHER PUBLICATIONS

Patani, George A., Bioisosterism: A rational approach in drug design, Chem. Rev. 96 (1996) 3147-3176.*
U.S. Appl. No. 10/599,046, filed Dec. 13, 2007, David W. Old.
U.S. Appl. No. 11/553,143, filed Jun. 7, 2007, Yariv Donde.
U.S. Appl. No. 11/774,411, filed May 22, 2008, David W. Old.
U.S. Appl. No. 11/775,283, filed Jan. 17, 2008, David W. Old.
Silverman: "Prodrugs and Drug Delivery Systems," Organic Chem. of Drug Design and Drug Action, 2d ed., 2004, pp. 496-557.

* cited by examiner

*Primary Examiner*—Kamal A Saeed
*Assistant Examiner*—Samantha L Shterengarts
(74) *Attorney, Agent, or Firm*—John E. Wurst; Kevin J. Forrestal; Allergan, Inc.

(57) ABSTRACT

Disclosed herein is a compound having a formula

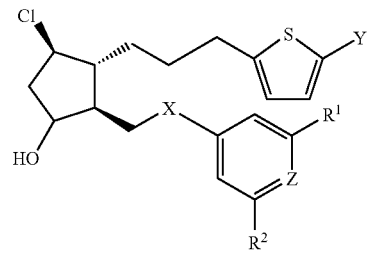

therapeutic methods, compositions, and medicaments related thereto are also disclosed.

16 Claims, No Drawings

THERAPEUTIC SUBSTITUTED CHLOROCYCLOPENTANOLS

RELATED APPLICATION

This application claims the benefit of U.S. Provisional Application Ser. No. 60/949,627, filed Jul. 13, 2007, which is hereby incorporated by reference in its entirety.

BACKGROUND

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

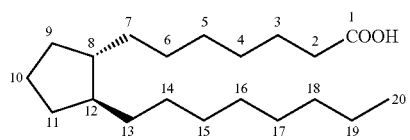

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

DESCRIPTION OF THE INVENTION

Disclosed herein is a compound having a formula

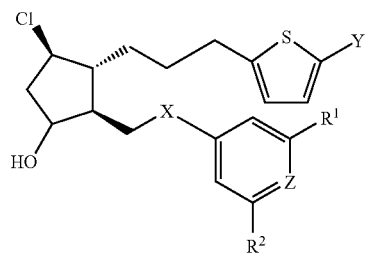

wherein Y is $CO_2H$ or $CH_2OH$;

X is $CH_2$, S, SO, or NH;

Z is CH or N; and $R^1$ and $R^2$ are independently F, Cl, methyl, or hydroxymethyl.

These compounds are useful for the treatment of glaucoma and the reduction of intraocular pressure. The compound is incorporated into a dosage form or a medicament and administered to the mammal, such as a person, in need thereof. For example, a liquid composition may be administered as an eye drop or a solid or liquid dosage form may also be administered orally. Other types of dosage forms and medicaments are well known in the art, and may also be used.

Another embodiment is a composition comprising a compound disclosed herein, wherein said composition is a liquid which is ophthalmically acceptable.

Another embodiment is a medicament comprising a compound disclosed herein, wherein said medicament is a liquid which is ophthalmically acceptable.

Another embodiment is a method comprising administering a compound disclosed herein to a mammal for the treatment of glaucoma or elevated intraocular pressure.

Another embodiment is a kit comprising a composition comprising compound disclosed herein, a container, and instructions for administration of said composition to a mammal for the treatment of glaucoma or elevated intraocular pressure.

Methods of formulating compounds such as those disclosed herein for ophthalmic and other pharmaceutical preparations are well known in the art. For example, U.S. patent application Ser. No. 10/599,046, filed on Sep. 18, 2006, incorporated by reference herein, describes typical formulation methods.

For the purposes of this disclosure, "treat," "treating," or "treatment" refer to the use of a compound, composition, therapeutically active agent, or drug in the diagnosis, cure, mitigation, treatment, or prevention of disease or other undesirable condition.

Unless otherwise indicated, reference to a compound should be construed broadly to include pharmaceutically acceptable salts, prodrugs, tautomers, alternate solid forms, non-covalent complexes, and combinations thereof, of a chemical entity of the depicted structure or chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids), one or more protonated basic groups (e.g. amines), or both (e.g. zwitterions).

A prodrug is a compound which is converted to a therapeutically active compound after administration. For example, conversion may occur by hydrolysis of an ester group or some other biologically labile group. Prodrug preparation is well known in the art. For example, "Prodrugs and Drug Delivery Systems," which is a chapter in Richard B. Silverman, *Organic Chemistry of Drug Design and Drug Action,* 2d Ed., Elsevier Academic Press: Amsterdam, 2004, pp. 496-557, provides further detail on the subject.

Tautomers are isomers that are in rapid equilibrium with one another. For example, tautomers may be related by transfer of a proton, hydrogen atom, or hydride ion.

Unless stereochemistry is explicitly depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

These compounds were prepared as described in U.S. patent Ser. No. 11/774,411, filed Jul. 6, 2007, incorporated by reference herein and U.S. patent Ser. No. 11/775,283, filed Jul. 10, 2007, incorporated by reference herein.

In Vitro Testing

U.S. patent application Ser. No. 11/553,143, filed on Oct. 26, 2006, incorporated by reference herein, describes the methods used to obtain the in vitro data in the tables below.

TABLE 1

| Structure | EP2 data | | | EP4 data | | Other Receptors (EC50 in nM) | | | | | |
|---|---|---|---|---|---|---|---|---|---|---|---|
| | flipr EC50 | cAMP EC50 | KI | flipr EC50 | KI | hFP | hEP1 | hEP3A | hTP | hIP | hDP |
| | 20 | 0.09 | 1.5 | 5583 | 678 | NA | NA | 7140 | NA | NA | NA |
| | 59 | 0.11 | 0.3 | >10000 | 828 | NA | NA | NA | NA | NA | NA |

TABLE 1-continued
| Structure | EP2 data | | | EP4 data | | Other Receptors (EC50 in nM) | | | | | |
|---|---|---|---|---|---|---|---|---|---|---|---|
| | flipr | cAMP | | flipr | | | | | | | |
| | EC50 | EC50 | KI | EC50 | KI | hFP | hEP1 | hEP3A | hTP | hIP | hDP |
| 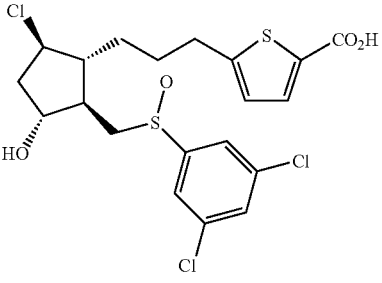 | 101 | 0.4 | 12 | NT | >1000 | NA | NA | NA | 4209 | NA | NA |
| 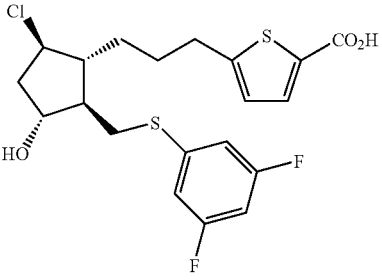 | 850 | 1.3 | 9 | >10000 | 2332 | NA | NA | NA | 5314 | NA | 9693 |
TABLE 2
| Structure | EP2 data | | | EP4 data | | Other Receptors (EC50 in nM) | | | | | |
|---|---|---|---|---|---|---|---|---|---|---|---|
| | flipr | cAMP | | flipr | | | | | | | |
| | EC50 | EC50 | Ki | EC50 | KI | hFP | hEP1 | hEP3A | hTP | hIP | hDP |
| 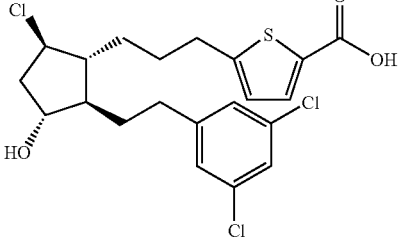 | 18 | 0.09 | 0.2 | >10000 | 616 | NA | NA | NA | >10000 | NA | NA |
| 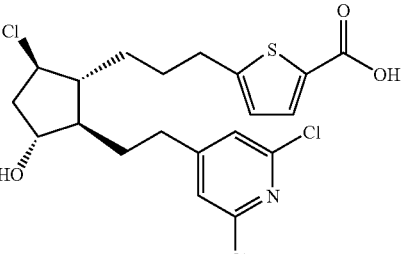 | 13 | 0.05 | 1 | >10000 | 582 | NA | NA | NA | NA | NA | NA |

TABLE 2-continued

| Structure | EP2 data | | | EP4 data | | Other Receptors (EC50 in nM) | | | | | |
|---|---|---|---|---|---|---|---|---|---|---|---|
| | flipr EC50 | cAMP EC50 | Ki | flipr EC50 | KI | hFP | hEP1 | hEP3A | hTP | hIP | hDP |
| [structure] | 86 | 0.08 | 1 | >10000 | 437 | NA | NA | NA | NA | NA | 2942 |
| [structure] | 10 | 0.1 | 2 | >10000 | 2572 | NA | NA | 8542 | 64 | NA | 12670 |
| [structure] | 287 | 0.4 | 3 | >10000 | 966 | NA | NA | NA | NA | NA | 15292 |
| [structure] | 10193 | 284 | 502 | NT | >10000 | NA | NA | NA | NA | NA | NA |
| [structure] | 501 | 4 | 22 | NT | >10000 | >10000 | NA | >10000 | NA | NA | >10000 |

IN VIVO EXAMPLES

U.S. Pat. No. 7,091,231 describes the methods used for these in vivo tests.

Example 1

5-(3-((1R,2R,3R,5R)-5-chloro-2-((3,5-dichlorophenylthio)methyl)-3-hydroxycyclopentyl)propyl)-thiophene-2-carboxylic acid was tested in normotensive dogs at 0.01%, dosing once daily for 5 days. The maximum intraocular pressure (IOP) decrease from baseline was 6.3 mmHg (35%) at 6 h; the maximum ocular surface hyperemia (OSH) score was 1.7 at 52 h.

Example 2

The composition and dosage regimen of example 1 was also tested in laser-induced hypertensive monkeys, using one single day dose. At 0.01%, the maximum IOP decrease from baseline was 13.9 mmHg (40%) at 24 h.

Example 3

The composition and dosage regimen of example 1 may also be used to reduce IOP in humans.

Example 4

7-{(1R,2R,3R,5R)-5-Chloro-2-[2-(3,5-dichloro-phenyl)-ethyl]-3-hydroxy-cyclopentyl}-heptanoic acid was tested in normotensive dogs at 0.01%, dosing once daily for 5 days. The maximum intraocular pressure (IOP) decrease from baseline was 3.6 mmHg (18%) at 102 h; the maximum ocular surface hyperemia (OSH) score was 0.8 at 74 h.

Example 5

The composition of Example 4 may be used to reduce IOP in a person by administering the composition once a day to the person.

Example 6

5-(3-((1R,2R,3R,5R)-5-chloro-2-(3,5-dichlorophenethyl)-3-hydroxycyclopentyl)propyl)thiophene-2-carboxylic acid was tested in normotensive dogs multiple concentrations, dosing once daily for 5 days. At 0.01%, the maximum intraocular pressure (IOP) decrease from baseline was 8.8 mmHg (47%) at 28 h; the maximum ocular surface hyperemia (OSH) score was 2.5 at 26 h. At 0.001%, the maximum intraocular pressure (IOP) decrease from baseline was 6.2 mmHg (34%) at 54 h; the maximum ocular surface hyperemia (OSH) score was 1.8 at 50 h. At 0.0005%, the maximum intraocular pressure (IOP) decrease from baseline was 5.6 mmHg (36%) at 54 h; the maximum ocular surface hyperemia (OSH) score was 1.75 at 50 h. At 0.0001%, the maximum intraocular pressure (IOP) decrease from baseline was 3.6 mmHg (24%) at 76 h; the maximum ocular surface hyperemia (OSH) score was 0.8 at 74 h.

Example 7

5-(3-((1R,2R,3R,5R)-5-chloro-2-(3,5-dichlorophenethyl)-3-hydroxycyclopentyl)propyl)thiophene-2-carboxylic acid was tested in laser-induced hypertensive monkeys, using one single day dose. At 0.01%, the maximum IOP decrease from baseline was 20.6 mmHg (55%) at 24 h.

Example 8

The compositions of Example 6 may be used to reduce IOP in a person by administering the composition once a day to the person.

Example 9

5-(3-((1R,2R,3R,5R)-5-chloro-2-(2-(2,6-dichloropyridin-4-yl)ethyl)-3-hydroxycyclopentyl)propyl)-thiophene-2-carboxylic acid (11b) was tested in normotensive dogs at 0.001%, dosing once daily for 4 days. The maximum intraocular pressure (IOP) decrease from baseline was 7.1 mmHg (36%) at 78 h; the maximum ocular surface hyperemia (OSH) score was 1.9 at 74 h. This compound was also tested in laser-induced hypertensive monkeys, using one single day dose. At 0.001%, the maximum IOP decrease from baseline was 12.6 mmHg (31%) at 24 h.

Example 10

The compositions of Example 9 may be used to reduce IOP in a person by administering the composition once a day to the person.

Example 11

5-(3-((1R,2R,3R,5R)-5-chloro-2-(3-chloro-5-(hydroxymethyl)phenethyl)-3-hydroxycyclopentyl)propyl)thiophene-2-carboxylic acid (11c) was tested in normotensive dogs at 0.001%, dosing once daily for 5 days. The maximum intraocular pressure (IOP) decrease from baseline was 2.2 mmHg (12%) at 30 h; the maximum ocular surface hyperemia (OSH) score was 0.8 at 50 h.

Example 12

The compositions of Example 11 may be used to reduce IOP in a person by administering the composition once a day to the person.

Example 13

Isopropyl 5-(3-((1R,2R,3R,5R)-5-chloro-2-(3-chloro-5-(hydroxymethyl)phenethyl)-3-hydroxycyclopentyl)propyl)thiophene-2-carboxylate was tested in normotensive dogs at 0.001%, dosing once daily for 5 days. The maximum intraocular pressure (IOP) decrease from baseline was 2.8 mmHg (17%) at 4 h; the maximum ocular surface hyperemia (OSH) score was 0.9 at 26 h.

Example 14

Isopropyl 5-(3-((1R,2R,3R,5R)-5-chloro-2-(3-chloro-5-(hydroxymethyl)phenethyl)-3-hydroxycyclopentyl)propyl)thiophene-2-carboxylate was also tested in laser-induced hypertensive monkeys, using one single day dose. At 0.001%, the maximum IOP decrease from baseline was 9.2 mmHg (24%) at 24 h.

Example 15

5-(3-((1R,2S,3R,5R)-5-chloro-2-((3,5-dichlorophenylamino)methyl)-3-hydroxycyclopentyl)propyl)thiophene-2- carboxylic acid was tested in normotensive dogs at 0.001%, dosing once daily for 5 days. The maximum intraocular pressure (IOP) decrease from baseline was 2.6 mmHg (18%) at 6 h; the maximum ocular surface hyperemia (OSH) score was 1.5 at 76 h. This compound was also tested in laser-induced hypertensive monkeys, using one single day dose. At 0.001%, the maximum IOP decrease from baseline was 6 mmHg (16%) at 6 h.

Example 16

5-(3-(((1R,2R,3R,5R)-5-chloro-2-((3,5-dichlorophenyl-sulfinyl)methyl)-3-hydroxycyclopentyl)propyl)thiophene-2-carboxylic acid was tested in normotensive dogs at 0.005%, dosing once daily for 5 days. The maximum intraocular pressure (IOP) decrease from baseline was 3.1 mmHg (21%) at 4 h; the maximum ocular surface hyperemia (OSH) score was 1.4 at 30 h.

Example 17

The compositions of Examples 1-16 may be used to reduce IOP in a person by administering the composition once a day to the person.

What is claimed is:
1. A compound having a formula

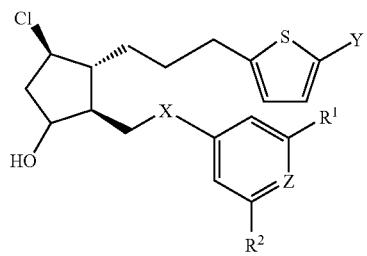

wherein Y is CO$_2$H or CH$_2$OH;
X is CH$_2$, S, SO, NH, or NCOCH$_3$;
Z is CH or N; and
R$^1$ and R$^2$ are independently F, Cl, methyl, or hydroxymethyl.

2. The compound of claim 1 selected from:

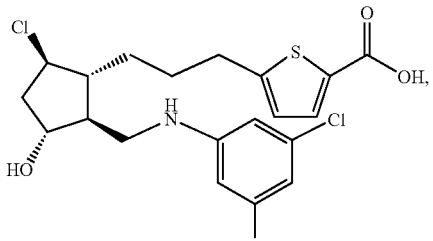

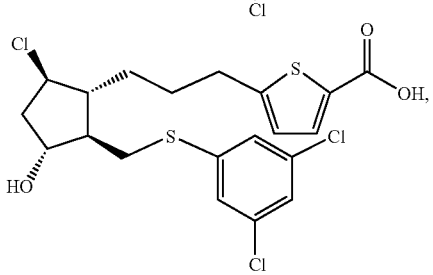

-continued

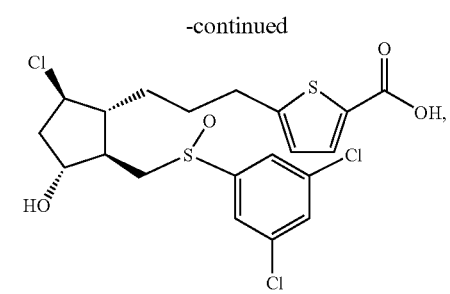

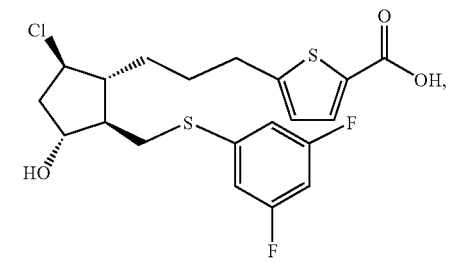

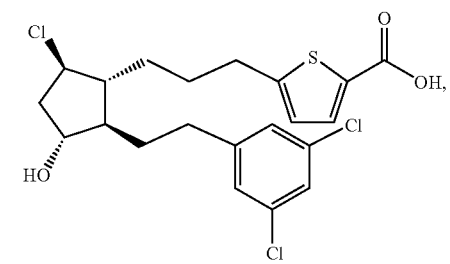

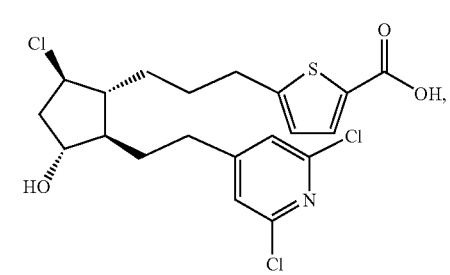

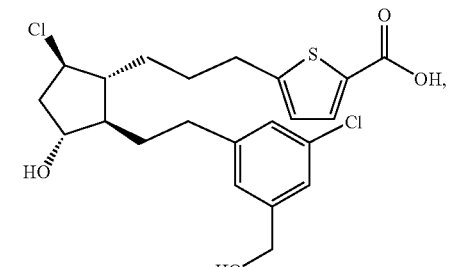

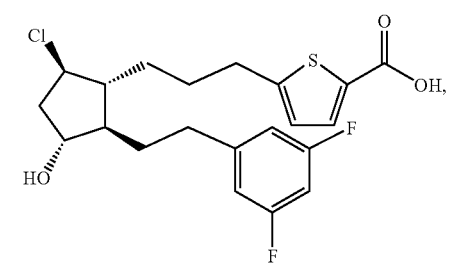

-continued
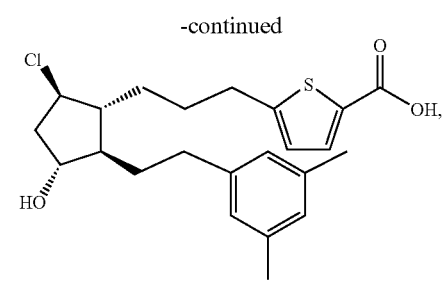
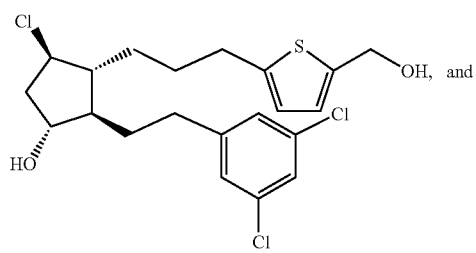
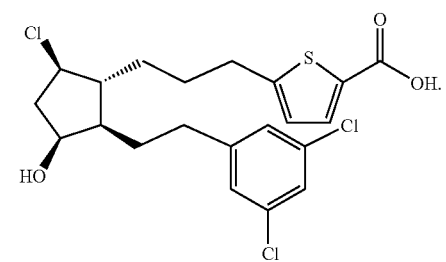
3. The compound of claim 2 having a formula:
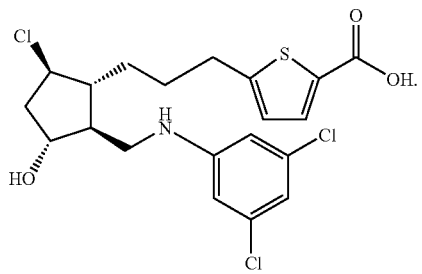
4. The compound of claim 2 having a formula:
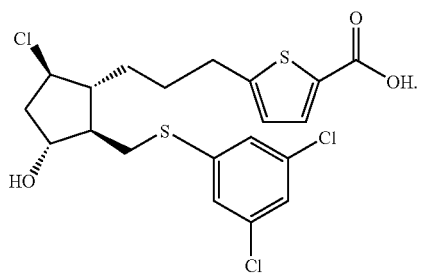
5. The compound of claim 2 having a formula:
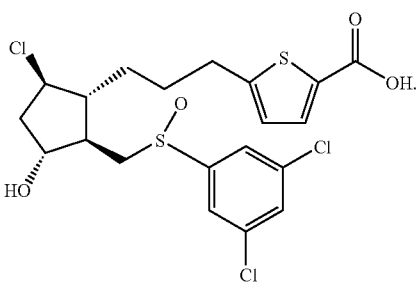
6. The compound of claim 2 having a formula:
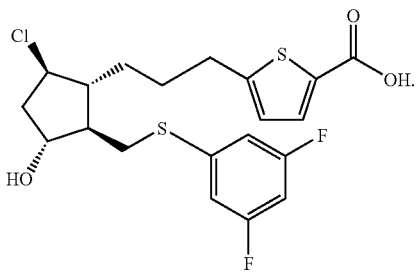
7. The compound of claim 2 having a formula:
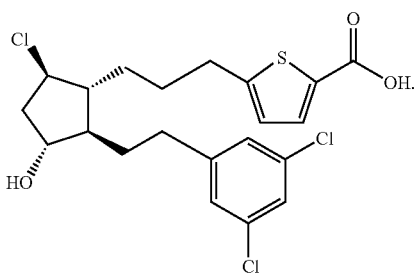
8. The compound of claim 2 having a formula:
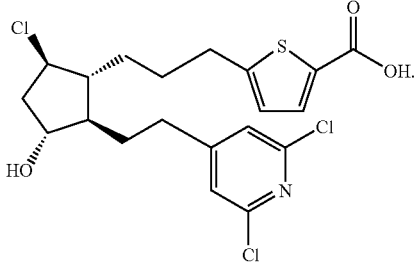

9. The compound of claim 2 having a formula:

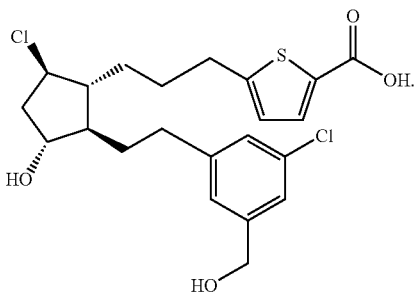

10. The compound of claim 2 having a formula:

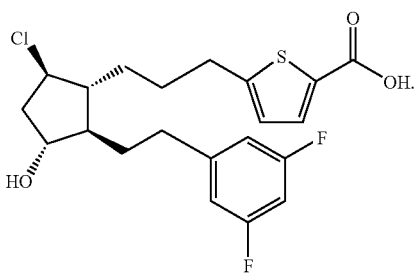

11. The compound of claim 2 having a formula:

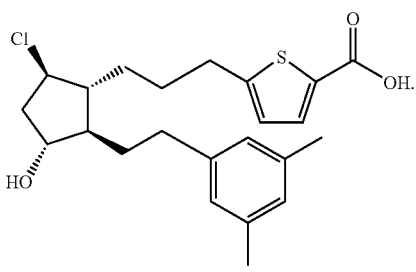

12. The compound of claim 2 having a formula:

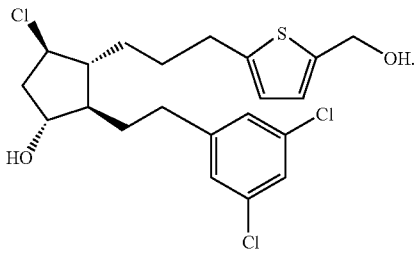

13. The compound of claim 2 having a formula:

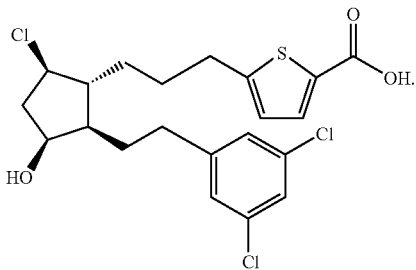

14. A method of reducing intraocular pressure comprising administering a compound of claim 1 to a mammal in need thereof.

15. A method of treating glaucoma comprising administering a compound of claim 1 to a mammal in need thereof.

16. A composition comprising a compound of claim 1 wherein said composition is a liquid which is ophthalmically acceptable.

* * * * *